United States Patent
Mukouyama et al.

(10) Patent No.: US 6,214,589 B1
(45) Date of Patent: *Apr. 10, 2001

(54) METHOD FOR PRODUCING L-ASPARTIC ACID

(75) Inventors: Masaharu Mukouyama; Satomi Komatsuzaki, both of Ibaraki (JP)

(73) Assignee: Nippon Shokubai Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/249,338

(22) Filed: Feb. 12, 1999

(30) Foreign Application Priority Data

Feb. 13, 1998 (JP) .................................................. 10-031809

(51) Int. Cl.$^7$ ...................................................... C12P 13/20
(52) U.S. Cl. ........................... 435/109; 435/177; 435/180; 435/232; 435/252.3
(58) Field of Search ..................................... 435/109, 177, 435/180, 232, 252.31, 252.33, 320.1; 536/23.2

(56) References Cited

U.S. PATENT DOCUMENTS

| 4,138,292 | 2/1979 | Chibata et al. | 195/59 |
| 5,962,280 | 10/1999 | Mukouyama et al. | 435/109 |

FOREIGN PATENT DOCUMENTS

| 0 110 422 A2 | 6/1984 | (EP) . |
| 0 110 422 A3 | 7/1985 | (EP) . |
| 55-35110 | 9/1980 | (JP) . |
| 3-48795 | 7/1991 | (JP) . |
| 10286087 | 10/1998 | (JP) . |

OTHER PUBLICATIONS

Chibata et al., Continuous Production of L–Aspartic Acid, Applied Biochemistry and Biotechnology, vol. 13 (1986), 231–240.

Chibata et al., Immobilized Aspartase–Containing Microbial Cells: Preparation and Enzymatic Properties, Applied Microbiology, vol. 27, No. 5 (1974), 878–885.

Takagi et al., Cloning and Nucleotide Sequence of the Aspartase Gene of Pseudomonas fluorescens, J. Biochem., vol. 100 (1986), 697–705.

Tosa et al., Basic Studies for Continuous Production of L–Aspartic Acid by Immobilized *Escherichia coli* Cells, Applied Microbiology, vol. 27, No. 5 (1974), 886–889.

Woods et al., Structural and Functional Relationships Between Fumarase and Aspartase, Biochem. J., vol. 237 (1986), 547–557.

Yokote et al., Production of L–Aspartic Acid by *E. coli* Aspartase Immobilized on Phenol–Formaldehyde Resin, J. of Solid–Phase Biochemistry, vol. 3, No. 4 (1978), 247–261.

Yukawa et al., Production of L–Aspartic Acid by Reusing Cells, J. of Japan Society for Bioscience, Biotechnology, and Agrochemistry, vol. 59, No. 1 (1985), 31–37.

Kawabata et al. "Continuous production of L–aspartic acid from ammonium fumarate using Immobilized cell. . . ." J. Ferm. Bioengin. 79, 317–322, 1995.*

\* cited by examiner

*Primary Examiner*—Nashaat T. Nashed
(74) *Attorney, Agent, or Firm*—Finnegan, Henderson, Farabow, Garrett & Dunner, L.L.P.

(57) ABSTRACT

This invention relates to a method for producing L-aspartic acid, comprising the steps of: immobilizing microbial cells containing aspartase to produce an immobilized aspartase; feeding an ammonium fumarate solution into a reactor filled with the immobilized aspartase; and recovering the produced L-aspartic acid from the reaction mixture, wherein the immobilized aspartase has an activity of 250 U or more, and wherein the ammonium fumarate solution is fed into the reactor at the feed rate LHSV of 2 to 35.

7 Claims, No Drawings

METHOD FOR PRODUCING L-ASPARTIC ACID

FIELD OF THE INVENTION

The present invention relates to a method for producing L-aspartic acid by using a microorganism with high aspartase activity.

BACKGROUND OF THE INVENTION

A method for enzymatically producing L-aspartic acid from ammonium fumarate by using a microorganism with aspartase activity, *Escherichia coli*, is known. Japanese Patent Publication No. 55-35110 (i.e., JP-B-55-35110) describes a method in which *E.coli* aspartase is immobilized on an ion-exchange resin Duolite A-7. Applied Biochemistry and Biotechnology vol. 13, pp.231–240 (1986) describes a method for continuously producing L-aspartic acid wherein a reactor is filled with *E.coli* cells immobilized in κ-carrageenan by gel entrapment. These methods, however, are unsatisfactory in terms of industrial productivity since the immobilized aspartase has a low activity or since the gel entrapment immobilization causes diffusion barrier or rate-limiting diffusion.

Since conventional immobilized aspartases do not have a sufficiently high activity, the reaction has to be carried out at 30° C. or higher, in which case cooling is required because aspartase loses its activity by heat of reaction. Particularly, the activity is remarkably decreased at a temperature exceeding 40° C. (Applied Microbiology vol. 27, No. 5, pp.878–885 (1974); Applied Microbiology vol. 27, No. 5, pp. 886–889 (1974)). To prevent a rise in temperature in a reactor caused by heat of reaction, the reactor needs to be equipped with an internal cooling tube or a cooling device such as jacket, which renders the reactor complicate. Further, prior art immobilized aspartases cannot be used to carry out enzymatic reactions at a high LHSV due to their low activities. In methods that use aspartases immobilized by gel entrapment, it is also impossible to carry out an enzymatic reaction at a high LHSV (Liquid Hour Space Velocity) since diffusion barrier becomes greater.

The reaction at high LHSV is required to achieve the improved productivity of L-aspartic acid by the enzymatic reaction using immobilized aspartases. Such a reaction can be realized with an immobilized aspartase which has a sufficiently high activity to react at a low temperature and which leads to a low diffusion barrier and a low pressure loss. Unfortunately, such an immobilized aspartase has not yet been prepared in the art. In this situation, the present inventors have now prepared an immobilized aspartase with the above preferable properties and have now found that the reaction at high LHSV is achieved substantially without removing heat by introducing a substrate solution into a reactor while controlling a temperature of the substrate solution to be lower than a temperature of impairing the stability of aspartase by at least a rise in a temperature caused by heat of reaction, thereby ensuring the stable activity of the immobilized aspartase.

SUMMARY OF THE INVENTION

The present invention provides a method for producing L-aspartic acid, comprising the steps of: immobilizing microbial cells containing aspartase to produce an immobilized aspartase; feeding an ammonium fumarate solution into a reactor filled with the immobilized aspartase; and recovering the produced L-aspartic acid from the reaction mixture, wherein the immobilized aspartase has an activity of 250 U or more, and wherein the ammonium fumarate solution is fed into the reactor at the feed rate LHSV of 2 to 35. As used herein, "1U" means 1 μmole L-aspartic acid yielded per minute per milliliter of immobilized enzyme, and "LHSV" stands for "Liquid Hour Space Velocity" and refers to a volume of feeding substrate (in ml) per volume of filled catalyst (in ml) per hour.

The immobilized aspartase usable in the invention is, for example, an immobilized recombinant microbial cell with an aspartase gene introduced using recombinant DNA techniques.

The immobilized aspartase can be obtained by coating a spherical carrier with the above-mentioned microbial cell containing aspartase in combination with a polymer. More specifically, the immobilized aspartase can be obtained by coating a spherical styrene divinylbenzene copolymer type ion-exchange resin carrier with the above-mentioned aspartase-containing microbial cells admixed with a polymer represented by the general formula:

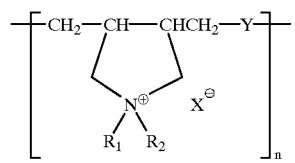

wherein Y is either a direct bond or a bifunctional group represented by the formula:

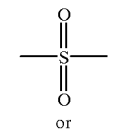

or

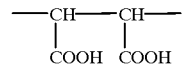

$R_1$ and $R_2$ are each independently a hydrogen atom or an organic residue, $X^\ominus$ is an anion, and n is a number between 100 to 5000.

Exemplary organic residues include alkyl groups with not less than 10 carbon atoms, such as methyl, ethyl, n-propyl, isopropyl, n-butyl, isobutyl and ter-butyl groups, preferably methyl group. The organic residues may include at least one halogen or hydroxyl group as a substituent and such examples are 4-chloro-2-dimethylpentyl group, 3-ethyl-2,5-dichloroheptyl group and 2-hydroxy-3,5-dimethylnonyl group, preferably 3-chloro-2-hydroxypropyl group.

Examples of $X^\ominus$ include halogen ions such as $F^-$, $Cl^-$, $Br^-$ and $I^-$, preferably $Cl^-$. Other monovalent anions, such as $NO_3^-$, may also be used as $X^\ominus$.

The immobilized aspartase of this invention obtained by immobilizing the above-described recombinant microbial cell containing an aspartase gene by the above-described immobilization method has an extremely high activity and leads to a low pressure loss as well as to a low diffusion barrier. As a result, unlike the conventional immobilized aspartases, it becomes possible to carry out an enzymatic reaction at a high LHSV by using the immobilized aspartase of the invention.

Since an ammonium fumarate solution at a low temperature can be fed for the reaction, a lifetime of aspartase can be extended.

These and other advantages of the present invention will become apparent to those skilled in the art upon reading and understanding the following detailed description.

This specification includes all or part of the contents as disclosed in the specification of Japanese Patent Application No. 10-31809 which is a priority document of the present application.

DETAILED DESCRIPTION OF THE INVENTION

An aspartase-containing microorganism that can be used with the present invention is preferably *Escherichia coli*, *Pseudomonas fluorescens*, the genus Brevibacterium or the like, which are known to have a high aspartase activity. In particular, a recombinant cell having an aspartase gene introduced by recombinant DNA techniques is preferred.

Preferably, the aspartase gene used with the present invention can be obtained from *E.coli* and a microorganism which has an aspartase activity and whose gene is known to naturally cross with an *E.coli* gene, for example, *Pseudomonas fluorescens*, the genus Enterobacter, or the genus Citrobacter. However, an aspartase gene from any microorganism with aspartase activity can suitably be used.

For example, aspartase genes may be amplified by PCR using the chromosomal DNA from *E.coli* K-12 (IFO3301) or *Pseudomonas fluorescens* (IFO3081) as a template and primers prepared based on the known aspartase gene sequence. Alternatively, aspartase genes may also be obtained by other usual methods such as the method where restriction fragments obtained from chromosomal DNA are electrophoresed to recover a fragment containing an aspartase gene.

A plasmid for incorporating the thus-obtained aspartase gene may be any plasmid that is capable of replicating in the cell of *E.coli*. Examples of such plasmids include, but are not limited to, pUC18 (Nippon Gene Co., Ltd.) and pKK223-3 (Pharmacia).

As a host microorganism for introducing the plasmid into which the aspartase gene has been incorporated, *E. coli* strain K-12 (Stratagene) or the like can suitably be used.

The aspartase-containing microbial cell is preferably immobilized by a method that gives a sufficient strength of the immobilized product and is less likely to cause pressure loss or diffusion barrier upon feeding a substrate solution.

Preferably, the microbial cell is immobilized by coating the surface of a spherical carrier with the cell and a polymer. More preferably, the surface of a styrene divinylbenzene copolymer type ion-exchange resin is coated with a mixture of the cell and polyallylamine polymer. As the styrene divinylbenzene copolymer type ion-exchange resin and the polyallylamine polymer, Amberlite IRA96SB (Organo) and PAS-880 (Nitto Boseki Co., Ltd.) are preferable, respectively.

According to the above-described method, since the aspartase-containing microbial cells per se can directly be immobilized on a carrier, the aspartase contained in the cells is almost entirely immobilized, thereby obtaining an immobilized aspartase with very high activity.

The microbial cells may be immobilized, by adding the cells admixed with PAS-880 (with a pH adjusted to 7.0) to an egg-plant-shaped flask containing Teflon balls and Amberlite IRA-96SB, and drying the mixture in a rotary evaporator under a reduced pressure while rotating, thereby coating the surface of Amberlite IRA-96SB with the cells and PAS-880.

According to the above-described method, spherical immobilized products are obtained whose pressure loss is 2.0 kg/cm$^2$ or less per meter of the length of an immobilized aspartase layer (in water, at 20° C.) when LHSV is 20. By this, a reaction at a high LHSV becomes possible. Further advantage of this method is that the diffusion layer is thin enough to exhibit a sufficient enzyme activity. The pressure loss of the immobilized enzyme is preferably 2 kg/cm$^2$ or less, more preferably 1 kg/cm$^2$ or less, per meter of a length of the immobilized aspartase layer when LHSV is 20. The shape of a reactor used with the present invention is usually, but not limited to, a cylindrical reactor. The length of the reactor is preferably 10 m or less because an excessively long reactor is responsible for pressure loss. There is no need of equipping the reactor with a cooling device. More preferably, the reactor is insulated.

It is necessary to set up a temperature controllable storage tank or a heat-exchanger ahead of the reactor so as to maintain the ammonium fumarate solution that is to be fed into the reactor at a constant temperature.

Generally, at a temperature exceeding 40° C., an enzyme of a mesophile is unstable and its inactivation is accelerated by heat. The aspartase of *E.coli* also shows drastic instability at a temperature exceeding 40° C. and loses its activity by heat (Applied Microbiology vol. 27, No. 5, pp. 878–885 (1974); Applied Microbiology vol. 27, No. 5, pp.886–889 (1974)). This inactivation by heat results in shortening the lifetime of the immobilized enzyme.

To prevent the inactivation of aspartase by heat, it is important to control the temperature of the ammonium fumarate solution to be fed into a reactor so that the temperature of the reaction mixture at the outlet of the reactor does not exceed 40° C.

Within such a range of temperature, good stability of the aspartase is obtained. In the case of *E.coli*, the range is 40° C. or less, and the stability is higher at a lower temperature. To attain a similar effect in an aspartase enzyme stable at an elevated temperature with an optimum temperature at 40° C. or higher, the temperature of a substrate solution to be fed is controlled to be lower than a temperature of impairing the stability of aspartase by at least a rise in the temperature caused by heat of reaction. The reaction at a temperature within the above-described range cannot be realized with conventional immobilized enzymes because their activities are insufficient. "The temperature of impairing the stability of aspartase" is around 40° C. in the case of aspartase from *E.coli*, around 48° C. in the case of aspartase from *Brevibacterium flavum* (Journal of Japan Society for Bioscience, Biotechnology, and Agrochemistry, vol. 59, No. 1, pp.31–37, 1985), and around 50° C. in the case of aspartase from Bacillus aminogenes (Japanese Patent Publication No. 3-48795).

Again, when an ammonium fumarate solution is fed into a reactor and converted into L-aspartic acid in an equilibrium state, the temperature of the ammonium fumarate solution will become higher. In this case, the temperature of the reaction mixture can be maintained at 40° C. or lower by controlling the temperature of an ammonium fumarate solution to be lower than 40° C. by at least a rise in temperature caused by heat of reaction. The temperature is preferably set as low as possible within the above range so that the stability is enhanced. However, an excessively low temperature may cause precipitation of the crystal ammonium fumarate, and thus the temperature of the ammonium fumarate solution at the inlet of the reactor is preferably in the range of 10° C. at the lowest to 33° C., more preferably 15° C. to 28° C.

Aspartases of microorganisms other than *E.coli* may be placed under conditions similar to the above.

More specifically, when the concentration of the ammonium fumarate solution is 10% (calculated as fumaric acid), the temperature rises by about 7° C. due to heat of reaction. Considering the reactivity of the immobilized aspartase, the ammonium fumarate solution is preferably fed into a reactor at a temperature of 10° C. to 33° C., more preferably 15° C. to 28° C.

When the concentration of the ammonium fumarate solution is 20% (calculated as fumaric acid), the temperature rises by about 14° C. due to heat of reaction and so the ammonium fumarate solution is suitably fed into a reactor at a temperature of 10° C. to 26° C., more preferably 15° C. to 24° C. In this manner, the temperature of the reaction mixture will not exceed 40° C. at the outlet of the reactor, and aspartase remains stable. Moreover, since there is no need of cooling in the reactor, the structure of the reactor itself may be simplified.

The velocity of the ammonium fumarate solution fed into a reactor is preferably as high as possible in view of productivity but it may be varied depending upon a concentration of the ammonium fumarate solution, an activity of the immobilized aspartase, and a length of the immobilized aspartase layer. LHSV is preferably in the range of 2 to 35, particularly 6 to 30, more preferably 7 to 25.

LHSV beyond the above-mentioned range is unfavorable because the conversion rate of ammonium fumarate into L-aspartic acid may become lower. On the other hand, LHSV below the above-mentioned ranges is also unfavorable because it causes low productivity.

The conversion rate of ammonium fumarate into L-aspartic acid at the outlet of a reactor is preferably 90% or higher, more preferably 95% or higher. Unusually low conversion rate is unfavorable since it increases the amount of unreactive fumaric acid and causes an increase in the cost.

Preferably, the immobilized aspartase has an activity of 250 U, more preferably 500 U.

When the activity of the immobilized aspartase is 250 U, the conversion rate is 99% or more under the conditions where 20% ammonium fumarate solution is fed into the reactor at LHSV of 2 and where the temperature at the inlet is 20° C. However, when the activity of the immobilized aspartase is 100 U and the other conditions are the same as above, the conversion rate drops to 80%. When the activity of the immobilized aspartase is 1,000 U, the conversion rate is 99% or more under the conditions where 20% ammonium fumarate solution is fed into the reactor at LHSV=10 and where the temperature at the inlet is 23° C.

As described above, the immobilized aspartase with higher activity enables the reaction at a higher LHSV.

Hereinafter, a method for preparing aspartase from *E.coli* or *Pseudomonas fluorescens* via genetic engineering techniques will be described.

(1) Preparation of Recombinant *E.coli* Aspartase

*E.coli* strain IFO3301 purchased from Institute for Fermentation, Osaka, Japan (IFO) was inoculated to an LB medium shown in Table 1, and cultured at 37° C. for 8 hours. From 1 ml of the culture, the *E.coli* cells were collected and suspended in 1 ml of distilled water. One µl of the cell suspension was used as a template DNA for amplifying an aspartase gene.

TABLE 1

| Composition of the LB medium | |
|---|---|
| Polypeptone | 10 g |
| Yeast extract | 5 g |
| NaCl | 10 g |
| Distilled water | 1 L (sterilized in an autoclave for 15 min at 121° C.) |

(2) Amplification of Aspartase Gene by PCR and Preparation of Insert Fragment

To amplify an aspartase gene from *E.coli*, the following two primers:

Primer F1:  GGATAATCGTCGGTCGAAAA  (SEQ ID NO:3), and

Primer R1:  CGTCATCTGACGTGCCTTT   (SEQ ID NO:4)

were prepared on the basis of the aspartase gene from known *E.coli* strain K-12 (whose nucleotide sequence is represented by SEQ ID NO:1 and the amino acid sequence encoded thereby by SEQ ID NO:2) (Biochem. J. 237(2), 547–557).

A reaction solution having the following composition was prepared using KOD DNA polymerase (Toyobo Co., Ltd.) to amplify the aspartase gene by PCR under the following conditions:

| Composition: | |
|---|---|
| 10 × Buffer | 5 µl |
| dNTPs Mix | 5 µl |
| $MgCl_2$ | 2 µl |
| Template DNA | 1 µl |
| KOD DNA polymerase | 1 µl |
| Primer F1 (25 pmol) | 1 µl |
| Primer R1 (25 pmol) | 1 µl |
| Sterilized water | 34 µl |
| Total | 50 µl |

PCR conditions (where ii. through iv. are repeated for 30 cycles):
  i. 98° C., 5 min.
  ii. 98° C., 30 sec.
  iii. 53° C., 30 sec.
  iv. 68° C., 1 min.

At the end of the PCR reaction, the amplified DNA fragments were electrophoresed on 1% agarose gel and stained with ethidium bromide. The predicted fragment of about 1600 bp was amplified.

The fragment was excised from the agarose gel to recover DNA with Prep-A-Gene® (Bio-Rad Laboratories, Inc.).

(3) Ligation of Insert Fragment to Vector

The recovered DNA fragment was ligated into pCR-Script Amp SK (+) cloning vector in the presence of a restriction enzyme Srf and a DNA ligase.

One transformant with the insert fragment was named the strain PUaspEl. The strain PUaspE1 was inoculated to 3 ml of LB medium containing 100 ppm ampicillin and shake cultured overnight at 37° C. From 1.5 ml of the culture, the cells were collected, and the plasmid was in turn recovered from the cells by alkaline SDS method. The plasmid was named pUaspE1.

Sequencing of the insert fragment in the plasmid revealed that the aspartase gene was inserted in a reverse direction relative to the promoter of the vector.

To correctly ligate the aspartase gene in a forward direction relative to the promoter, the insert fragment was cleaved out from plasmid pUaspE1 with restriction enzymes SacI and BamHI to be introduced into pUC19 (Nippon Gene Co., Ltd.). Specifically, plasmid pUaspE1 was first cleaved with BamHI and then DNA was collected by ethanol precipitation prior to another cleavage with SacI. The cleaved DNA fragments were separated through electrophoresis on 1% agarose gel and excised from the gel to recover the DNA insert with Prep-A-Gene® (Bio-Rad Laboratories, Inc.).

(4) Preparation of Vector

One μg of plasmid pUC19 (Nippon Gene Co., Ltd.) was cleaved with the restriction enzyme BamHI, and then the resulting DNA was recovered by ethanol precipitation and cleaved with SacI. The cleaved DNA fragments were separated through electrophoresis on 1% agarose gel and excised from the gel to recover the target DNA as a vector using Prep-A-Gene® (Bio-Rad Laboratories, Inc.).

(5) Ligation of Insert Fragment to Vector

The insert fragment and the vector, which both had been cleaved with the same restriction enzymes, were ligated together using Ligation highs (Toyobo Co., Ltd.) for 30 minutes at 16° C.

(6) Transformation of *E.coli*

To transform *E.coli*, 2 μl of the reaction mixture containing the vector with the insert fragment ligated was added to 200 μl of competent *E. coli* cells (XL2-Blue MRF' ultracompetent cells produced by Stratagene). The *E.coli* transformant was spread over an LB agar medium containing 100 ppm of ampicillin and cultured overnight at 37° C.

As a control, *E.coli* transformed with plasmid pUC18 with no insert fragment was spread over an LB agar medium containing 100 ppm of ampicillin and cultured overnight at 37° C.

Twenty of the presented colonies were picked up, inoculated to an LB medium containing 100 ppm ampicillin, and shake cultured at 37° C. After 8 hours, IPTG (isopropyl-1-thio-β-D-galactoside) was added to the culture to a concentration of 1 mM and the shake culture was further continued overnight at 30° C. From 1 ml of the culture, the cells were recovered.

Similarly, one control transformant with no insert fragment was cultured to recover the cells. The recovered cells were suspended by adding 1 ml of an ammonium fumarate substrate solution shown in Table 2 and left to react for 1 hour at 30° C.

TABLE 2

| Composition of 20% ammonium fumarate substrate solution | |
| --- | --- |
| Fumaric acid | 200 g |
| 25% Aqueous ammonia | 200 g |
| Magnesium sulfate | 2.5 g |
| Ion exchange water | 500 g |

After adjusting the pH of the reaction mixture to 8.3 with 25% aqueous ammonia, ion exchange water was added to give 1 L in total. When the reaction mixture was analyzed, the % conversion into L-aspartic acid in the *E.coli* transformant with the insert fragment was 99.5%, whereas the % conversion in the control transformant with no insert fragment was 5%.

One transformant with the insert fragment was named PUaspE2. The strain PUaspE2 was inoculated to 3 ml LB medium containing 100 ppm ampicillin, and cultured for 8 hours at 37° C. From 1.5 ml of the culture, the plasmid was recovered by alkaline SDS method, which was named pUaspE2. Plasmid pUaspE2 was cleaved with the restriction enzyme SmaI, subsequently with the restriction enzyme HindIII, and were subjected to 1% agarose gel electrophoresis to determine the size of the DNA fragments. Two fragments with sizes of about 2960 bp and about 1600 bp were present.

The strain PUaspE2 was inoculated to 3 ml LB medium containing 100 ppm ampicillin and shake cultured at 37° C. After 8 hours, IPTG was added to the culture to a concentration of 1 mM and the shake culture was further continued overnight at 30° C. From 1 ml of the culture, the cells were recovered and the density thereof was 8.0 as determined at OD 660 nm. The cells were suspended in 10 ml of 20% ammonium fumarate substrate solution and were left to react for 1 hour at 30° C. The reaction mixture was analyzed by HPLC. Aspartase activity was calculated based on the L-aspartic acid yield and the cell density, which turned out to be 2,000,000 μM L-aspartic acid yield/hr/OD 660 nm cell density.

Similarly, one control transformant with no insert fragment was cultured and recovered. The density thereof was 8.5 as determined at OD 660 nm. The cells were suspended in 10 ml of 20% ammonium fumarate substrate solution and reacted for 1 hour at 30° C. The reaction mixture was analyzed by HPLC. Aspartase activity was calculated based on the L-aspartic acid yield and the cell density, which turned out to be 10,000 μM L-aspartic acid yield/hr/OD 660 nm cell density.

The aspartase activity of the strain PUaspE2 was 200 times greater than that of the strain with no aspartase gene insert.

(7) Cultivation of Recombinant *E.coli*

Recombinant *E.coli* strain PUaspE2 capable of expressing *E.coli* aspartase was inoculated to 10 test tubes each containing 3 ml of a medium prepared by adding 100 ppm ampicillin to the medium shown in Table 1, and cultured at 37° C. After 8 hours, the cultures in the test tubes were respectively inoculated to 10 Sakaguchi flasks each containing 100 ml of a medium consisting of the same composition as the above medium supplemented with 1 mM IPTG, and then shake cultured overnight at 30° C.

From these cultures, the cells were collected by centrifugation. Aspartase activity measured of the cells was 1.05 moles L-aspartic acid yield/hr per gram of the cells.

(8) Preparation of Recombinant *Pseudomonas fluorescens* Aspartase

*Pseudomonas fluorescens* strain IFO3081 purchased from Institute for Fermentation, Osaka (IFO) was inoculated to the LB medium shown in Table 1 and cultured at 30° C. for 8 hours. From 1 ml of the culture, the cells were collected and suspended in 1 ml of distilled water. One μl of the cell suspension was used as a template DNA for amplifying an aspartase gene.

(9) Amplification of Aspartase Gene by PCR and Preparation of Insert Fragment

To amplify an aspartase gene from *Pseudomonas fluorescens*, the following two primers:

```
Primer F2:  GGGCATATGATCTCCGTCATGTCCTCTGCTGCATCTTTCCG  (SEQ ID NO:5),
and
Primer R2:  CCCGGATCCTTAGGCCTTCAGCGGACCAAGCGTGGGG      (SEQ ID NO:6)
``` were prepared on the basis of the nucleotide sequence of the aspartase gene from known *Pseudomonas fluorescens* strain IFO3081 (J.Biochem. 100, 697–705 (1986)).

A reaction solution having the following composition was prepared using KOD DNA polymerase (Toyobo Co., Ltd.) to amplify the aspartase gene by PCR under the following conditions:

| Composition: | |
|---|---|
| 10 × Buffer | 5 μl |
| dNTPs Mix | 5 μl |
| MgCl$_2$ | 2 μl |
| Template DNA | 1 μl |
| KOD DNA polymerase | 1 μl |
| Primer F2 (25 pmol) | 1 μl |
| Primer R2 (25 pmol) | 1 μl |
| Sterilized water | 34 μl |
| Total | 50 μl |

PCR conditions (where ii. through iv. are repeated for 30 cycles):

i. 98° C., 5 min.
ii. 98° C., 30 sec.
iii. 55° C., 30 sec.
iv. 68° C., 1 min.

At the end of the PCR reaction, the amplified DNA fragments were electrophoresed on 1% agarose gel and stained with ethidium bromide. The predicted fragment of about 1500 bp was amplified.

The target fragment was excised from the agarose gel to recover DNA with Prep-A-Gene® (Bio-Rad Laboratories Inc.). The recovered DNA was cleaved simultaneously with restriction enzymes NdeI and BamHI, and the resulting NdeI-BamHI fragment was separated by electrophoresis on 1% agarose gel and excised from the gel to recover the DNA using Prep-A-Gene® (Bio-Rad Laboratories Inc.) as described above.

(10) Preparation of Vector

To prepare, through PCR, a vector DNA fragment which has NdeI and BamHI restriction enzyme sites at positions of initiation and termination codons, respectively, of the structural gene for β-galactosidase of plasmid pUC18, the following two primers:

```
Primer F3:  CCCCATATGTGTTTCCTGTGTGAAATTGTTATCCGCTCACA  (SEQ ID NO:7), and
            ATTCCACACAATATACGAGCC
Primer R3:  CCCGGATCCTTAGTTAAGCCAGCCCCGACACCCGCCAACACC  (SEQ ID NO:8)
``` were prepared.

A reaction solution having the following composition was prepared using KOD DNA polymerase (Toyobo Co., Ltd.) to amplify the aspartase gene by PCR and, as a template DNA, plasmid pUC18 was used:

| Composition: | |
|---|---|
| 10 × Buffer | 5 μl |
| dNTPs Mix | 5 μl |
| MgCl$_2$ | 2 μl |
| Template DNA | 1 μl |
| KOD DNA polymerase | 1 μl |
| Primer F3 (25 pmol) | 1 μl |
| Primer R3 (25 pmol) | 1 μl |
| Sterilized water | 34 μl |
| Total | 50 μl |

PCR conditions (where ii. through iv. are repeated for 30 cycles):

i. 98° C., 5 min.
ii. 98° C., 30 sec.
iii. 55° C., 30 sec.
iv. 68° C., 1 min.

At the end of the PCR reaction, the amplified DNA fragments were electrophoresed on 1% agarose gel and stained with ethidium bromide. The predicted fragment of about 2400 bp was amplified.

The target fragment was excised from the agarose gel to recover DNA with Prep-A-Gene® (Bio-Rad Laboratories Inc.). The recovered DNA was cleaved simultaneously with restriction enzymes NdeI and BamHI, the resulting NdeI-BamHI fragment was separated by electrophoresis on 1% agarose gel and excised from the gel to recover the DNA as a vector DNA using Prep-A-Gene® (Bio-Rad Laboratories Inc.) as described above.

(11) Ligation of Insert Fragment to Vector

The vector and the insert fragment, which had been cleaved with the same restriction enzymes, were ligated together using Ligation high® (Toyobo Co., Ltd.) for 30 minutes at 16° C.

(12) Transformation of *E.coli*

To transform *E. coli*, 2 μl of the reaction mixture containing the vector with insert fragment ligated was added to 200 μl of competent *E.coli* cells (XL2-Blue MRF' ultracompetent cells produced by Stratagene). The *E.coli* transformant was spread over an LB agar medium containing 100 ppm of ampicillin and cultured overnight at 37° C.

As a control, *E.coli* transformed with plasmid pUC18 with no insert fragment was spread over the same LB agar medium containing 100 ppm of ampicillin and cultured overnight at 37° C.

Twenty of the presented colonies were picked up, inoculated to an LB medium containing 100 ppm ampicillin, and shake cultured at 37° C. After 8 hours, IPTG was added to the culture to a concentration of 1 mM and the shake culture was further continued overnight at 30° C. From 1 ml of the culture, the cells were recovered.

Similarly, one control transformant with no insert fragment was cultured to recover the cells.

The recovered cells were suspended in 1 ml of the ammonium fumarate substrate solution shown in Table 2 and left to react for 1 hour at 30° C.

The reaction mixture was analyzed. As a result, the % conversion into L-aspartic acid in the *E.coli* transformant with the insert fragment was 99.5%, whereas the % conversion in the control transformant with no insert fragment was 5%.

One transformant with the insert fragment was named PUaspP1. The strain PUaspP1 was inoculated to 3 ml LB medium containing 100 ppm ampicillin, and cultured for 8 hours at 37° C. From 1.5 ml of the culture, the plasmid was recovered by alkaline SDS method, which was named pUaspP1. The plasmid was cleaved with restriction enzymes NdeI and BamHI and then subjected to 1% agarose gel electrophoresis to determine the size of the DNA fragments. Two fragments with sizes of about 2400 bp and about 1500 bp were present.

The strain PUaspP1 was inoculated to 3 ml LB medium containing 100 ppm ampicillin and shake cultured at 37° C. After 8 hours, IPTG was added to the culture to a concentration of 1 mM and the shake culture was further continued overnight at 30° C. From 1 ml of the culture, the cells were collected and the density thereof was 8.0 as determined at OD 660 nm. The cells were suspended in 10 ml of 20% ammonium fumarate substrate solution and were left to react for 1 hour at 30° C. The reaction mixture was analyzed by HPLC. Aspartase activity was calculated based on the L-aspartic acid yield and the cell density, which turned out to be 2,500,000 $\mu$M L-aspartic acid yield/hr/OD 660 nm cell density.

Similarly, one control transformant with no insert fragment was cultured and recovered. The density thereof was 7.0 as determined at OD 660 nm. The cells were suspended in 10 ml of 20% ammonium fumarate substrate solution and reacted for 1 hour at 30° C. The reaction mixture was analyzed by HPLC. Aspartase activity was calculated based on the L-aspartic acid yield and the cell density, which turned out to be 10,000 $\mu$M L-aspartic acid yield/hr/OD 660 nm cell density.

The aspartase activity of the strain pUaspP1 was 250 times greater than that of the strain with no aspartase gene insert.

(13) Cultivation of Recombinant *E.coli*

Recombinant *E.coli* strain pUaspP1 capable of expressing *Pseudomonas fluorescens* aspartase was inoculated to 10 test tubes each containing 3 ml of a medium prepared by adding 100 ppm ampicillin to the medium shown in Table 1, and cultured at 37° C. After 8 hours, the cultures in the test tubes were respectively inoculated to 10 Sakaguchi flasks each containing 100 ml of a medium consisting of the same composition as the above medium supplemented with 1 mM IPTG, and then shake cultured overnight at 30° C.

From these cultures, the cells were collected by centrifugation. Aspartase activity measured of the cells was 0.85 moles L-aspartic acid yield/hr per gram of the cells.

Hereinafter, the present invention will be described in more detail by the following examples. The technical scope of the present invention, however, is not limited to the examples.

EXAMPLE 1

Recombinant *E.coli* strain pUaspP1 capable of expressing *Pseudomonas fluorescens* aspartase was inoculated to 10 test tubes each containing 3 ml of a medium prepared by adding 100 ppm ampicillin to the medium shown in Table 1, and cultured at 37° C. After 8 hours, the cultures in the test tubes were respectively inoculated to 10 Sakaguchi flasks each containing 100 ml of a medium prepared by adding 1 mM IPTG and 100 ppm ampicillin to the medium shown in Table 3, and shake cultured overnight at 30° C. From these cultures, the cells were collected by centrifugation. Aspartase activity was 0.19 moles L-aspartic acid yield/hr per gram of the cells.

Table 3

| Composition of medium | |
|---|---|
| Fumaric acid | 10 g |
| Ammonium sulfate | 5 g |
| KH$_2$PO$_4$ | 1 g |
| K$_2$HPO$_4$ | 3 g |
| MgSO$_4$.7H$_2$O | 0.5 g |
| NaOH | 6.5 g, pH 6.3 |
| Yeast extract | 20 g |
| (sterilized in an autoclave for 15 min at 121° C.) | |

70 g of PAS-880 (Nitto Boseki Co., Ltd.) (having pH of around 7.0 adjusted with alkali) and 230 g deionized water were mixed thoroughly, in which the collected cells were dispersed homogeneously. 300 ml of an ion exchange resin (Amberlite IRA-96SB type C1 produced by Organo, Japan, average particle size 0.5 mm) and 200 Teflon balls (0.5 inch each) were put in a 6 L egg-plant shaped flask, to which one sixth of the above-obtained cell dispersion was added. The mixture was dried for 1 hour in an evaporator while rotating at 30° C. to thereby coat the ion exchange resin with the cells. After repeating this step 6 times, the Teflon balls were removed to obtain a bead-like immobilized aspartase. The immobilized aspartase had an activity of 354 U.

The immobilized aspartase prepared as described above was immersed in 20% ammonium fumarate solution (pH 8.3) overnight at 4° C., 50 ml of which was used to fill a columnar reactor (1 cm diameter). The length of the loaded immobilized aspartase layer was about 64 cm. To insulate the reactor from heat, the column was covered with a thermally insulating material, i.e., polystyrene foam. A substrate solution (200 g fumaric acid, 200 g 25% aqueous ammonia, 0.25 g MgSO$_4$.7 H$_2$O in 1 L; pH 8.3 adjusted with aqueous ammonia) was fed into the column via a Teflon tube covered with a thermally insulating material at a flow rate of 100 ml/hr (LHSV=2.0) to carry out a continuous reaction.

Three hours after the beginning of the reaction, the reaction mixture was analyzed. The moles of the obtained reaction product, i.e., L-aspartic acid, substantially equaled the moles of the consumed fumaric acid. The reaction conversion rate was 99.77%. The temperature of the efflux was 33° C. The conversion rate remained at 99.7% seven days and even one month after the beginning of the reaction.

To measure a pressure loss of the immobilized aspartase, water (20° C.) was allowed to flow through the column. As a result, the pressure loss was 0.8 kg/cm$^2$ per meter of the length of an immobilized aspartase layer when LHSV is 20 (1 L/hr).

EXAMPLE 2

Recombinant *E.coli* strain PUaspP1 capable of expressing *Pseudomonas fluorescens* aspartase was inoculated to 10 test tubes each containing 3 ml of a medium prepared by adding 100 ppm ampicillin to the medium shown in Table 1, and cultured at 37° C. After 8 hours, the cultures in the test tubes were respectively inoculated to 10 Sakaguchi flasks each containing 100 ml of a medium prepared by adding 1 mM IPTG and 100 ppm ampicillin to the medium shown in Table 3, and shake cultured overnight at 30° C. From these cultures, the cells were collected by centrifugation. Aspartase activity was 0.85 moles L-aspartic acid yield/hr per gram of the cells.

The cells were immobilized in the same manner as in Example 1 to obtain an immobilized aspartase. The activity of the immobilized aspartase was 2800 U.

The immobilized aspartase so prepared was immersed in 20% ammonium fumarate solution (pH 8.3) overnight at 4° C., 10 ml of which was used to fill a columnar reactor (1 cm diameter) to carry out a continuous reaction as described in Example 1. The length of the loaded immobilized aspartase layer was about 13 cm. A substrate solution (20° C.) was fed at a flow rate of 100 ml/hr (LHSV=10.0).

Three hours after the beginning of the reaction, the reaction mixture was analyzed. The moles of the obtained reaction product, i.e., L-aspartic acid, substantially equaled the moles of the consumed fumaric acid. The reaction conversion rate was 99.6%. The temperature of the efflux was 33° C. The conversion rate remained at 99.5% seven days and even one month after the beginning of the reaction.

EXAMPLE 3

Recombinant *E.coli* strain PUaspP1 capable of expressing *Pseudomonas fluorescens* aspartase was inoculated to 10 test tubes each containing 3 ml of a medium prepared by adding 100 ppm ampicillin to the medium shown in Table 1, and cultured at 37° C. After 8 hours, the cultures in the test tubes were respectively inoculated to 10 Sakaguchi flasks each containing 100 ml of a medium prepared by adding 1 mM IPTG and 100 ppm ampicillin to the medium shown in Table 3, and shake cultured overnight at 30° C. From these cultures, the cells were collected by centrifugation. Aspartase activity was 0.85 moles L-aspartic acid yield/hr per gram of the cells.

The cells were immobilized as described in Example 1 to obtain an immobilized aspartase, except that only half of the cells were used for immobilization. The activity of the immobilized aspartase was 560 U.

The immobilized aspartase so prepared was immersed in 20% ammonium fumarate solution (pH 8.3) overnight at 4° C., 10 ml of which was used to fill a columnar reactor (1 cm diameter) to carry out a continuous reaction as described in Example 2 except that the substrate solution was maintained at 23° C. in a thermostat. The substrate solution was fed at a flow rate of 100 ml/hr (LHSV=10.0).

Three hours after the beginning of the reaction, the reaction mixture was analyzed. The moles of the obtained reaction product, i.e., L-aspartic acid, substantially equaled the moles of the consumed fumaric acid. The reaction conversion rate was 99.6%. The temperature of the efflux was 36° C. The conversion rate remained at 99.5% seven days and even one month after the beginning of the reaction.

EXAMPLE 4

Recombinant *E.coli* strain PUaspE2 capable of expressing *E.coli* aspartase was inoculated to 10 test tubes each containing 3 ml of medium prepared by adding 100 ppm ampicillin to the medium shown in Table 1, and cultured at 37° C. After 8 hours, the cultures in the test tubes were respectively inoculated to 10 Sakaguchi flasks each containing 100 ml of a medium prepared by adding 1 mM IPTG and 100 ppm ampicillin to the medium shown in Table 3, and shake cultured overnight at 30° C. From these cultures, the cells were collected by centrifugation. Aspartase activity was 1.27 moles L-aspartic acid yield/hr per gram of the cells.

The cells were immobilized in the same manner as in Example 1 to obtain an immobilized aspartase. The activity of the immobilized aspartase was 3200 U.

The immobilized aspartase so prepared was immersed in 20% ammonium fumarate solution (pH 8.3) overnight at 4° C., 10 ml of which was used to fill a columnar reactor (1 cm diameter) to carry out a continuous reaction as described in Example 1. A substrate solution (20° C.) was fed at a flow rate of 100 ml/hr (LHSV=10.0).

Three hours after the beginning of the reaction, the reaction mixture was analyzed. The moles of the obtained reaction product, i.e., L-aspartic acid, substantially equaled the moles of the consumed fumaric acid. The reaction conversion rate was 99.6%. The temperature of the efflux was 33° C. The conversion rate remained at 99.6% seven days and even one month after the beginning of the reaction.

To measure a pressure loss of the immobilized aspartase, water (20° C.) was allowed to flow through this column. As a result, the pressure loss was 0.7 $kg/cm^2$ per meter of the length of an immobilized aspartase layer when LHSV is 20 (1 L/hr).

EXAMPLE 5

Recombinant *E.coli* strain PUaspE2 capable of expressing *E.coli* aspartase was cultured to collect cells as described in Example 4. The aspartase activity was 1.00 mole L-aspartic acid yield/hr per gram of the cells. Immobilized aspartase was obtained as described in Example 1 except that only one tenth of the obtained cells were used. The activity of the immobilized aspartase was 265 U.

The immobilized aspartase so prepared was immersed in 20% ammonium fumarate solution (pH 8.3) overnight at 4° C., 10 ml of which was used to fill a columnar reactor (1 cm diameter) to carry out a continuous reaction as described in Example 1. A substrate solution (20° C.) was fed at a flow rate of 20 ml/hr (LHSV=2.0). Three hours after the beginning of the reaction, the reaction mixture was analyzed. The moles of the obtained reaction product, i.e., L-aspartic acid, substantially equaled the moles of the consumed fumaric acid. The reaction conversion rate was 99.2%. The temperature of the efflux was 31° C. The conversion rate remained at 99.2% seven days and even one month after the beginning of the reaction.

EXAMPLE 6

Recombinant *E. coli* strain PUaspE2 capable of expressing *E.coli* aspartase was cultured to collect cells as described in Example 4. The aspartase activity was 1.20 moles L-aspartic acid yield/hr per gram of the cells. From the cells, an immobilized aspartase was prepared as described in Example 1. The immobilized aspartase had an aspartase activity of 3600 U.

The immobilized aspartase so prepared was immersed in 20% ammonium fumarate solution (pH 8.3) overnight at 4° C., 10 ml of which was used to fill a columnar reactor (1 cm diameter) to carry out a continuous reaction as described in Example 1. A substrate solution (20° C.) was fed at a flow rate of 200 ml/hr (LHSV=20.0).

Three hours after the beginning of the reaction, the reaction mixture was analyzed. The moles of the obtained reaction product, i.e., L-aspartic acid, substantially equaled the moles of the consumed fumaric acid. The reaction conversion rate was 97.0%. The temperature of the efflux was 33° C. The conversion rate remained at 97.0% seven days and even one month after the beginning of the reaction.

EXAMPLE 7

Recombinant *E.coli* strain PUaspE2 capable of expressing *E.coli* aspartase was cultured to collect cells as described in Example 4. The aspartase activity was 1.20 moles L-aspartic acid yield/hr per gram of the cells. From the cells, an immobilized aspartase was prepared as described in Example 1. The immobilized aspartase had an activity of 3600 U.

The immobilized aspartase so prepared was immersed in 20% ammonium fumarate solution (pH 8.3) overnight at 4° C., 10 ml of which was used to fill a columnar reactor (1 cm diameter) to carry out a continuous reaction as described in Example 1. A substrate solution (20° C.) was fed at a flow rate of 250 ml/hr (LHSV=25.0).

Three hours after the beginning of the reaction, the reaction mixture was analyzed. The moles of the obtained reaction product, i.e., L-aspartic acid, substantially equaled the moles of the consumed fumaric acid. The reaction conversion rate was 90.0%. The temperature of the efflux was 31° C. The conversion rate remained at 90.0% seven days and even one month after the beginning of the reaction.

EXAMPLE 8

As described in Example 4, the recombinant *E.coli* strain PUaspE2 capable of expressing *E.coli* aspartase was cultured and subjected to the immobilization procedure twice to prepare about 600 ml of an immobilized aspartase. The immobilized aspartase had an aspartase activity of 3000 U. The immobilized aspartase so prepared was immersed in 20% ammonium fumarate solution (pH 8.3) for 1 week, 500 ml of which was used to fill a columnar reactor (1 inch diameter) to carry out a continuous reaction as described in Example 1. The length of the immobilized aspartase layer was 80 cm.

The reaction was carried out under the conditions where the temperature of the substrate solution was 24° C. and the feed rate was 5 L/hour (LHSV=10). Two hours after the beginning of the reaction, the reaction mixture was analyzed. The moles of the obtained reaction product, i.e., L-aspartic acid, substantially equaled the moles of the consumed fumaric acid. The reaction conversion rate was 99.4%.

Three hours after the beginning of the reaction, the feed rate was changed to 10 L/hr (LHSV=20). An hour later, the reaction mixture was analyzed. The moles of the obtained reaction product, i.e., L-aspartic acid, substantially equaled the moles of the consumed fumaric acid. The reaction conversion rate was 98.2%.

Five hours after the beginning of the reaction, the feed rate was changed to 12.5 L/hr (LHSV=25). An hour later, the reaction mixture was analyzed. The moles of the obtained reaction product, i.e., L-aspartic acid, substantially equaled the moles of the consumed fumaric acid. The reaction conversion rate was 96.3%.

Seven hours after the beginning of the reaction, the feed rate was changed to 15 L/hr (LHSV=30). An hour later, the reaction mixture was analyzed. The moles of the obtained reaction product, i.e., L-aspartic acid, substantially equaled the moles of the consumed fumaric acid. The reaction conversion rate was 93.8%.

Nine hours after the beginning of the reaction, the feed rate was changed to 17.5 L/hr (LHSV 35). An hour later, the reaction mixture was analyzed. The moles of the obtained reaction product, i.e., L-aspartic acid, substantially equaled the moles of the consumed fumaric acid. The reaction conversion rate was 90.3%.

Eleven hours after the beginning of the reaction, the feed rate was changed to 20 L/hr (LHSV=40). An hour later, the reaction mixture was analyzed. The moles of the obtained reaction product, i.e., L-aspartic acid, substantially equaled the moles of the consumed fumaric acid. The reaction conversion rate was 85.8%.

Comparative Example 1

*E.coli* strain K-12 (IFO3301) was inoculated to 10 test tubes each containing 3 ml of the medium shown in Table 3, and cultured at 37° C. After 8 hours, the cultures in the test tubes were respectively inoculated to 10 Sakaguchi flasks each containing 100 ml of the medium shown in Table 3, and shake cultured overnight at 30° C. From these cultures, the cells were collected by centrifugation. Aspartase activity was 0.063 moles L-aspartic acid yield/hr per gram of the cells. From the obtained cells, an immobilized aspartase was prepared as described in Example 1. The immobilized aspartase had an activity of 126 U.

The immobilized aspartase so prepared was immersed in 20% ammonium fumarate solution (pH 8.3) overnight at 4° C., 10 ml of which was used to fill a columnar reactor (1 cm diameter) to carry out a continuous reaction as described in Example 1. A substrate solution (20° C.) was fed at a flow rate of 20 ml/hr (LHSV=2.0).

Three hours after the beginning of the reaction, the reaction mixture was analyzed. The moles of the obtained reaction product, i.e., L-aspartic acid, substantially equaled the moles of the consumed fumaric acid. The reaction conversion rate was 86.4%. The temperature of the efflux was 31° C. The conversion rates were 86.8% and 86.2% seven days and one month after the beginning of the reaction, respectively.

Comparative Example 2

Recombinant *E.coli* strain PUaspE1 capable of expressing *E.coli* aspartase was cultured to prepare an immobilized aspartase as described in Example 5. The activity of the immobilized aspartase was 263 U.

A substrate solution (200 g fumaric acid, 200 g 25% aqueous ammonia, 0.25 g $MgSO_4 \cdot 7 H_2O$ in 1 L; pH 8.3 adjusted with aqueous ammonia) maintained at 30° C. in a thermostat was fed into a reactor at a flow rate of 20 ml/hr (LHSV=2.0) via a Teflon tube covered with a thermally insulating material to carry out a continuous reaction as described in Example 1.

Three hours after the beginning of the reaction, the reaction mixture was analyzed. The moles of the obtained reaction product, i.e., L-aspartic acid, substantially equaled the moles of the consumed fumaric acid. The reaction conversion rate was 99.7%. The temperature of the efflux was 43° C. The conversion rates were 94.5% and 77.6% seven days and one month after the beginning of the reaction, respectively.

Comparative Example 3

Recombinant *E.coli* strain PuaspE2 capable of expressing *E.coli* aspartase was cultured to collect cells as described in Example 4. The aspartase activity was 1.20 moles L-aspartic acid yield/hr per gram of the cells. From the obtained cells, an immobilized aspartase was prepared as described in Example 1. The immobilized aspartase had an activity of 3500 U.

The immobilized aspartase so prepared was immersed in 20% ammonium fumarate solution (pH 8.3) overnight at 4° C., 10 ml of which was used to fill a columnar reactor (1 cm diameter) to carry out continuous reaction as described in Example 1. A substrate solution (20° C.) was fed at a flow rate of 300 ml/hr (LHSV=30.0).

Three hours after the beginning of the reaction, the reaction mixture was analyzed. The moles of the obtained reaction product, i.e., L-aspartic acid, substantially equaled the moles of the consumed fumaric acid. The reaction conversion rate was 75.0%. The temperature of the efflux was 31° C. The conversion rate remained at 75.0% seven days and even one month after the beginning of the reaction.

According to the method of the present invention, L-aspartic acid can be obtained in a high yield by using a microorganism with high aspartase activity.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

All publications, including patent and patent application cited herein are incorporated herein by reference in their entirety.

What is claimed is:

1. A method for producing L-aspartic acid, comprising:
   a) immobilizing microbial cells containing aspartase to produce an immobilized aspartase;
   b) feeding an ammonium fumarate solution into a reactor filled with the immobilized aspartase; and
   c) recovering the produced L-aspartic acid from the reaction mixture, wherein the immobilized aspartase has an activity of 250 U (umole/min/mL immobilized aspartase) or more, and wherein the ammonium fumarate solution is fed into the reactor at the feed rate LHSV (Liquid Hour Space Velocity) of 2 to 35-hr$^{-1}$.

2. A method according to claim 1, wherein the temperature of the ammonium fumarate solution to be introduced into the reactor is set to be lower than a temperature that destabilizes the aspartase in order to offset the rise in temperature caused by the heat of reaction.

3. A method according to claim 1, wherein the temperature of the ammonium fumarate solution to be introduced into the reactor is in the range of 10 to 33° C.

4. A method according to claim 1, wherein the microbial cell containing aspartase is a recombinant microbial cell with an aspartase gene introduced by recombinant DNA techniques.

5. A method according to any one of claims 1 to 4, wherein the immobilized aspartase is obtained by coating a spherical carrier with a mixture comprising a water-soluble polyallylamine polymer and microbial cells containing aspartase.

6. A method according to any one of claims 1 to 4, wherein the immobilized aspartase is obtained by coating a spherical styrene-divinylbenzene copolymer type ion-exchange resin carrier with the aspartase-containing microbial cells admixed with a polymer represented by the general formula:

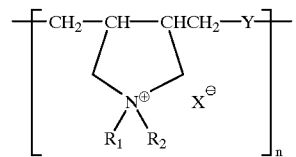

wherein Y is either a direct bond or a bifunctional group represented by the formula:

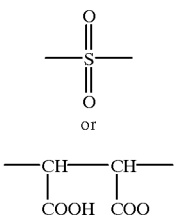

$R_1$ and $R_2$ are each independently a hydrogen atom or an organic residue, $X^{\ominus}$ is an anion, and n is a number between 100 to 5000.

7. A method according to any one of claims 1 to 4, wherein the pressure loss through the reactor is 2.0 kg/cm$^2$ or less per meter of a length of the immobilized aspartase layer, in water, at 20° C., when LHSV is 20 hr$^{-1}$.

* * * * *

SEQUENCE LISTING

<160> NUMBER OF SEQ ID NOS: 8

<210> SEQ ID NO 1
<211> LENGTH: 1573
<212> TYPE: DNA
<213> ORGANISM: Escherichia coli

<400> SEQUENCE: 1

```
ggggataatc gtcggtcgaa aaacattcga aaccacatat attctgtgtg tttaaagcaa        60
atcattggca gcttgaaaaa gaaggttcac atg tca aac aac att cgt atc gaa       114
                                  Met Ser Asn Asn Ile Arg Ile Glu
                                   1               5 gaa gat ctg ttg ggt acc agg gaa gtt cca gct gat gcc tac tat ggt        162
Glu Asp Leu Leu Gly Thr Arg Glu Val Pro Ala Asp Ala Tyr Tyr Gly
         10                  15                  20 gtt cac act ctg aga gcg att gta aac ttc tat atc agc aac aac aaa        210
Val His Thr Leu Arg Ala Ile Val Asn Phe Tyr Ile Ser Asn Asn Lys
 25                  30                  35                  40 atc agt gat att cct gaa ttt gtt cgc ggt atg gta atg gtt aaa aaa        258
Ile Ser Asp Ile Pro Glu Phe Val Arg Gly Met Val Met Val Lys Lys
                     45                  50                  55 gcc gca gct atg gca aac aaa gag ctg caa acc att cct aaa agt gta        306
Ala Ala Ala Met Ala Asn Lys Glu Leu Gln Thr Ile Pro Lys Ser Val
             60                  65                  70 gcg aat gcc atc att gcc gca tgt gat gaa gtc ctg aac aac gga aaa        354
Ala Asn Ala Ile Ile Ala Ala Cys Asp Glu Val Leu Asn Asn Gly Lys
         75                  80                  85 tgc atg gat cag ttc ccg gta gac gtc tac cag ggc ggc gca ggt act        402
Cys Met Asp Gln Phe Pro Val Asp Val Tyr Gln Gly Gly Ala Gly Thr
 90                  95                  100 tcc gta aac atg aac acc aac gaa gtg ctg gcc aat atc ggt ctg gaa        450
Ser Val Asn Met Asn Thr Asn Glu Val Leu Ala Asn Ile Gly Leu Glu
105                 110                 115                 120 ctg atg ggt cac caa aaa ggt gaa tat cag tac ctg aac ccg aac gac        498
Leu Met Gly His Gln Lys Gly Glu Tyr Gln Tyr Leu Asn Pro Asn Asp
                    125                 130                 135 cat gtt aac aaa tgt cag tcc act aac gac gcc tac ccg acc ggt ttc        546
His Val Asn Lys Cys Gln Ser Thr Asn Asp Ala Tyr Pro Thr Gly Phe
            140                 145                 150 cgt atc gca gtt tac tct tcc ctg att aag ctg gta gat gcg att aac        594
Arg Ile Ala Val Tyr Ser Ser Leu Ile Lys Leu Val Asp Ala Ile Asn
        155                 160                 165 caa ctg cgt gaa ggc ttt gaa cgt aaa gct gtc gaa ttc cag gac atc        642
Gln Leu Arg Glu Gly Phe Glu Arg Lys Ala Val Glu Phe Gln Asp Ile
    170                 175                 180
```

```
ctg aaa atg ggt cgt acc cag ctg cag gac gca gta ccg atg acc ctc      690
Leu Lys Met Gly Arg Thr Gln Leu Gln Asp Ala Val Pro Met Thr Leu
185                 190                 195                 200 ggt cag gaa ttc cgc gct ttc agc atc ctg ctg aaa gaa gaa gtg aaa      738
Gly Gln Glu Phe Arg Ala Phe Ser Ile Leu Leu Lys Glu Glu Val Lys
                205                 210                 215 aac atc caa cgt acc gct gaa ctg ctg ctg gaa gtt aac ctt ggt gca      786
Asn Ile Gln Arg Thr Ala Glu Leu Leu Leu Glu Val Asn Leu Gly Ala
            220                 225                 230 aca gca atc ggt act ggt ctg aac acg ccg aaa gag tac tct ccg ctg      834
Thr Ala Ile Gly Thr Gly Leu Asn Thr Pro Lys Glu Tyr Ser Pro Leu
                235                 240                 245 gca gtg aaa aaa ctg gct gaa gtt act ggc ttc cca tgc gta ccg gct      882
Ala Val Lys Lys Leu Ala Glu Val Thr Gly Phe Pro Cys Val Pro Ala
        250                 255                 260 gaa gac ctg atc gaa gcg acc tct gac tgc ggc gct tat gtt atg gtt      930
Glu Asp Leu Ile Glu Ala Thr Ser Asp Cys Gly Ala Tyr Val Met Val
265                 270                 275                 280 cac ggc gcg ctg aaa cgc ctg gct gtg aag atg tcc aaa atc tgt aac      978
His Gly Ala Leu Lys Arg Leu Ala Val Lys Met Ser Lys Ile Cys Asn
                285                 290                 295 gac ctg cgc ttg ctc tct tca ggc cca cgt gcc ggc ctg aac gag atc     1026
Asp Leu Arg Leu Leu Ser Ser Gly Pro Arg Ala Gly Leu Asn Glu Ile
            300                 305                 310 aac ctg ccg gaa ctg cag gcg ggc tct tcc atc atg cca gct aaa gta     1074
Asn Leu Pro Glu Leu Gln Ala Gly Ser Ser Ile Met Pro Ala Lys Val
                315                 320                 325 aac ccg gtt gtt ccg gaa gtg gtt aac cag gta tgc ttc aaa gtc atc     1122
Asn Pro Val Val Pro Glu Val Val Asn Gln Val Cys Phe Lys Val Ile
        330                 335                 340 ggt aac gac acc act gtt acc atg gca gca gaa gca ggt cag ctg cag     1170
Gly Asn Asp Thr Thr Val Thr Met Ala Ala Glu Ala Gly Gln Leu Gln
345                 350                 355                 360 ttg aac gtt atg gag ccg gtc att ggc cag gcc atg ttc gaa tcc gtt     1218
Leu Asn Val Met Glu Pro Val Ile Gly Gln Ala Met Phe Glu Ser Val
                365                 370                 375 cac att ctg acc aac gct tgc tac aac ctg ctg gaa aaa tgc att aac     1266
His Ile Leu Thr Asn Ala Cys Tyr Asn Leu Leu Glu Lys Cys Ile Asn
            380                 385                 390 ggc atc act gct aac aaa gaa gtg tgc gaa ggt tac gtt tac aac tct     1314
Gly Ile Thr Ala Asn Lys Glu Val Cys Glu Gly Tyr Val Tyr Asn Ser
                395                 400                 405 atc ggt atc gtt act tac ctg aac ccg ttc atc ggt cac cac aac ggt     1362
Ile Gly Ile Val Thr Tyr Leu Asn Pro Phe Ile Gly His His Asn Gly
        410                 415                 420 gac atc gtg ggt aaa atc tgt gcc gaa acc ggt aag agt gta cgt gaa     1410
Asp Ile Val Gly Lys Ile Cys Ala Glu Thr Gly Lys Ser Val Arg Glu
425                 430                 435                 440 gtc gtt ctg gaa cgc ggt ctg ttg act gaa gcg gaa ctt gac gat att     1458
Val Val Leu Glu Arg Gly Leu Leu Thr Glu Ala Glu Leu Asp Asp Ile
                445                 450                 455 ttc tcc gta cag aat ctg atg cac ccg gct tac aaa gca aaa cgc tat     1506
Phe Ser Val Gln Asn Leu Met His Pro Ala Tyr Lys Ala Lys Arg Tyr
            460                 465                 470 act gat gaa agc gaa cag taatcgtaca gggtagtaca aataaaaaag            1554
Thr Asp Glu Ser Glu Gln
                475 gcacgtcaga tgacgtgcc                                                1573
```

-continued

```
<210> SEQ ID NO 2
<211> LENGTH: 478
<212> TYPE: PRT
<213> ORGANISM: Escherichia coli

<400> SEQUENCE: 2

Met Ser Asn Asn Ile Arg Ile Glu Glu Asp Leu Leu Gly Thr Arg Glu
 1               5                  10                  15

Val Pro Ala Asp Ala Tyr Tyr Gly Val His Thr Leu Arg Ala Ile Val
            20                  25                  30

Asn Phe Tyr Ile Ser Asn Asn Lys Ile Ser Asp Ile Pro Glu Phe Val
        35                  40                  45

Arg Gly Met Val Met Val Lys Lys Ala Ala Met Ala Asn Lys Glu
    50                  55                  60

Leu Gln Thr Ile Pro Lys Ser Val Ala Asn Ala Ile Ile Ala Ala Cys
65                  70                  75                  80

Asp Glu Val Leu Asn Asn Gly Lys Cys Met Asp Gln Phe Pro Val Asp
                85                  90                  95

Val Tyr Gln Gly Gly Ala Gly Thr Ser Val Asn Met Asn Thr Asn Glu
            100                 105                 110

Val Leu Ala Asn Ile Gly Leu Glu Leu Met Gly His Gln Lys Gly Glu
        115                 120                 125

Tyr Gln Tyr Leu Asn Pro Asn Asp His Val Asn Lys Cys Gln Ser Thr
    130                 135                 140

Asn Asp Ala Tyr Pro Thr Gly Phe Arg Ile Ala Val Tyr Ser Ser Leu
145                 150                 155                 160

Ile Lys Leu Val Asp Ala Ile Asn Gln Leu Arg Glu Gly Phe Glu Arg
                165                 170                 175

Lys Ala Val Glu Phe Gln Asp Ile Leu Lys Met Gly Arg Thr Gln Leu
            180                 185                 190

Gln Asp Ala Val Pro Met Thr Leu Gly Gln Glu Phe Arg Ala Phe Ser
        195                 200                 205

Ile Leu Leu Lys Glu Glu Val Lys Asn Ile Gln Arg Thr Ala Glu Leu
    210                 215                 220

Leu Leu Glu Val Asn Leu Gly Ala Thr Ala Ile Gly Thr Gly Leu Asn
225                 230                 235                 240

Thr Pro Lys Glu Tyr Ser Pro Leu Ala Val Lys Lys Leu Ala Glu Val
                245                 250                 255

Thr Gly Phe Pro Cys Val Pro Ala Glu Asp Leu Ile Glu Ala Thr Ser
            260                 265                 270

Asp Cys Gly Ala Tyr Val Met Val His Gly Ala Leu Lys Arg Leu Ala
        275                 280                 285

Val Lys Met Ser Lys Ile Cys Asn Asp Leu Arg Leu Leu Ser Ser Gly
    290                 295                 300

Pro Arg Ala Gly Leu Asn Glu Ile Asn Leu Pro Glu Leu Gln Ala Gly
305                 310                 315                 320

Ser Ser Ile Met Pro Ala Lys Val Asn Pro Val Val Pro Glu Val Val
                325                 330                 335

Asn Gln Val Cys Phe Lys Val Ile Gly Asn Asp Thr Thr Val Thr Met
            340                 345                 350

Ala Ala Glu Ala Gly Gln Leu Gln Leu Asn Val Met Glu Pro Val Ile
        355                 360                 365

Gly Gln Ala Met Phe Glu Ser Val His Ile Leu Thr Asn Ala Cys Tyr
    370                 375                 380
```

```
Asn Leu Leu Glu Lys Cys Ile Asn Gly Ile Thr Ala Asn Lys Glu Val
385                 390                 395                 400

Cys Glu Gly Tyr Val Tyr Asn Ser Ile Gly Ile Val Thr Tyr Leu Asn
                405                 410                 415

Pro Phe Ile Gly His His Asn Gly Asp Ile Val Gly Lys Ile Cys Ala
            420                 425                 430

Glu Thr Gly Lys Ser Val Arg Glu Val Val Leu Glu Arg Gly Leu Leu
            435                 440                 445

Thr Glu Ala Glu Leu Asp Asp Ile Phe Ser Val Gln Asn Leu Met His
        450                 455                 460

Pro Ala Tyr Lys Ala Lys Arg Tyr Thr Asp Glu Ser Glu Gln
465                 470                 475

<210> SEQ ID NO 3
<211> LENGTH: 20
<212> TYPE: DNA
<213> ORGANISM: Artificial Sequence
<220> FEATURE:
<223> OTHER INFORMATION: Designed primer based on aspartase gene
      sequence of Escherichia coli K-12 strainiSEQ ID NO:1jD

<400> SEQUENCE: 3
ggataatcgt cggtcgaaaa                                              20

<210> SEQ ID NO 4
<211> LENGTH: 19
<212> TYPE: DNA
<213> ORGANISM: Artificial Sequence
<220> FEATURE:
<223> OTHER INFORMATION: Designed primer based on aspartase gene
      sequence of Escherichia coli K-12 strainiSEQ ID NO:1jD

<400> SEQUENCE: 4
cgtcatctga cgtgcctttt                                              19

<210> SEQ ID NO 5
<211> LENGTH: 41
<212> TYPE: DNA
<213> ORGANISM: Artificial Sequence
<220> FEATURE:
<223> OTHER INFORMATION: Designed primer based on aspartase gene
      sequence of Pseudomonas fluorescens IFO 3081 strainD

<400> SEQUENCE: 5
gggcatatga tctccgtcat gtcctctgct gcatctttcc g                      41

<210> SEQ ID NO 6
<211> LENGTH: 37
<212> TYPE: DNA
<213> ORGANISM: Artificial Sequence
<220> FEATURE:
<223> OTHER INFORMATION: Designed primer based on aspartase gene
      sequence of Pseudomonas fluorescens IFO 3081 strainD

<400> SEQUENCE: 6
cccggatcct taggccttca gcggaccaag cgtgggg                           37

<210> SEQ ID NO 7
<211> LENGTH: 62
<212> TYPE: DNA
<213> ORGANISM: Artificial Sequence
<220> FEATURE:
```

```
<223> OTHER INFORMATION: Designed primer to prepare vector DNA
      fragment by PCR which has NdeI restriction enzyme at initiation
      codon and BamHI restriction enzyme at termination codon of
      structural gene for beta-galactosidase of plasmid pUC18D

<400> SEQUENCE: 7
ccccatatgt gtttcctgtg tgaaattgtt atccgctcac aattccacac aatatacgac      60
cc                                                                    62

<210> SEQ ID NO 8
<211> LENGTH: 42
<212> TYPE: DNA
<213> ORGANISM: Artificial Sequence
<220> FEATURE:
<223> OTHER INFORMATION: Designed primer to prepare vector DNA fragment
      by PCR which has NdeI restriction enzyme at initiation codon and
      BamHI restriction enzyme at termination codon of structural gene
      for beta-galactosidase of plasmid pUC18D

<400> SEQUENCE: 8
cccggatcct tagttaagcc agccccgaca cccgccaaca cc                        42
```